United States Patent
Levine et al.

(10) Patent No.: US 10,300,106 B2
(45) Date of Patent: *May 28, 2019

(54) AUTOPHAGY-INDUCING PEPTIDE ANALOGS

(71) Applicants: Board of Regents, The University of Texas System, Austin, TX (US); Baylor College of Medicine, Houston, TX (US)

(72) Inventors: Beth C. Levine, Dallas, TX (US); Sanae Shoji-Kawata, Dallas, TX (US); Nick V. Grishin, Dallas, TX (US); Lisa N. Kinch, Dallas, TX (US); Olivier Lichtarge, Houston, TX (US); Angela D. Wilkins, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/844,007

(22) Filed: Sep. 3, 2015

(65) Prior Publication Data

US 2015/0359840 A1 Dec. 17, 2015

Related U.S. Application Data

(63) Continuation of application No. PCT/US2014/018467, filed on Feb. 26, 2014.

(60) Provisional application No. 61/803,095, filed on Mar. 18, 2013.

(51) Int. Cl.
| | | |
|---|---|---|
| *A61K 38/08* | (2019.01) | |
| *C07K 14/47* | (2006.01) | |
| *C07K 14/82* | (2006.01) | |
| *C07K 7/06* | (2006.01) | |

(52) U.S. Cl.
CPC ............... *A61K 38/08* (2013.01); *C07K 7/06* (2013.01); *C07K 14/47* (2013.01); *C07K 14/4747* (2013.01); *C07K 14/82* (2013.01)

(58) Field of Classification Search
CPC .... A61K 38/08; C07K 14/47; C07K 14/4747; C07K 14/82; C07K 7/06
USPC ................................ 514/21.6; 530/327, 328
See application file for complete search history.

(56) References Cited

U.S. PATENT DOCUMENTS

2013/0202646 A1* 8/2013 Gottlieb ............. C07K 14/4702
424/278.1

OTHER PUBLICATIONS

K7ERY0 from UniProt, pp. 1-6. Last sequence update Jan. 9, 2013.*
Conlan et al, "Circular Proteins and Mechanisms of Cyclization," Peptide Science, 2010, 94(5): 573-583.*
"Glycosylation" from Thermo Fisher Scientific, pp. 1-10. Accessed Jan. 23, 2019.*

* cited by examiner

*Primary Examiner* — Julie Ha
(74) *Attorney, Agent, or Firm* — Richard Aron Osman

(57) ABSTRACT

An autophagy-inducing compound comprises an autophagy-inducing peptide comprising Beclin 1 peptides immediately N- and C-terminally flanked by moieties $R_1$ and $R_2$, respectively, wherein up to six of said peptide residues may be substituted, $R_1$ and $R_2$ do not naturally flank the Beclin 1 residues, and F270 and F274 are optionally substituted and optionally linked. The compounds may be used to induce autophagy.

20 Claims, No Drawings
Specification includes a Sequence Listing.

AUTOPHAGY-INDUCING PEPTIDE ANALOGS

This is a continuation of PCT/US14/18467, filed Feb. 26, 2014, which claims priority to Ser No. 61/803,095, filed Mar. 18, 2013.

This invention was made with government support under Grant Number U54AI057156 awarded by the National Institutes of Health (NIH). The government has certain rights in the invention.

INTRODUCTION

Beclin 1 encodes a 450 amino acid protein with a central coiled coil domain. Within its N' terminus, it contains a BH3-only domain, which mediates binding to anti-apoptotic molecules such as Bcl-2 and Bcl-xL. The most highly conserved region, referred to as the evolutionarily conserved domain (ECD), spans from amino acids 244-337, which is important for its interaction with Vps34. Overexpression of Beclin 1 is sufficient to induce autophagy. Furuya, et al., *Autophagy* 1, 46-52, 2005; Pattingre, S. et al. *Cell* 122, 927-39, 2005.

We disclosed an autophagy-inducing beclin 1 peptide in PCT/US13/22350.

SUMMARY OF THE INVENTION

The invention provides methods and compositions for inducing autophagy, including compounds comprising no more than a 9, 10 or 11-mer Beclin 1 peptide (from residue 269 or 270 to residue 278 or 279).

In one aspect the invention is an autophagy-inducing compound comprising an autophagy-inducing peptide comprising Beclin 1 residue 269 or 279 to Beclin 1 residue 278 or 279, wherein Beclin 1 residues 269-279 is VFNATFHIWHS (SEQ ID NO:01), or the D-retro-inverso sequence thereof, wherein the peptide is immediately N- and C-terminally flanked by moieties $R_1$ and $R_2$, respectively, wherein up to six of said residues may be substituted, $R_1$ and $R_2$ do not naturally flank the Beclin 1 peptide, and F270 and F274 are optionally substituted and optionally linked.

In particular embodiments the invention is a subject autophagy-inducing compound, having a peptide sequence disclosed herein, unsubstituted, or wherein up to six of said residues may be substituted, and the two F residues are $F_1$ and $F_2$ and are optionally substituted and optionally linked, or the D-retro-inverso sequence of the peptide;

wherein $R_1$ is a heterologous moiety that promotes therapeutic stability or delivery of the compound;

wherein R1 comprises a transduction domain, a homing peptide, or a serum stabilizing agent;

wherein R1 is a tat protein transduction domain linked to the peptide through a diglycine linker, particularly a diglycine-T-N linker;

wherein $R_2$ is carboxyl;

wherein $R_2$ comprises an affinity tag or detectable label, particularly a fluorescent label;

wherein F270 and F274 are substituted and linked;

wherein F270 and F274 are substituted with crosslinkable moieties and/or linked, and each optionally comprises an additional α-carbon substitution selected from substituted, optionally hetero-lower alkyl, particularly optionally substituted, optionally hetero-methyl, ethyl, propyl and butyl;

wherein F270 and F274 are substituted with homocysteines connected through a disulfide bridge to generate a ring and tail cyclic peptide;

wherein the side chains of F270 and F274 are replaced by a linker:

—$(CH_2)_n$ONHCOX$(CH_2)_m$—, wherein X is $CH_2$, NH or O, and m and n are integers 1-4, forming a lactam peptide;

—$CH_2OCH_2CHCHCH_2OCH_2$—, forming an ether peptide; or

—$(CH_2)_n$CHCH$(CH_2)_m$—, forming a stapled peptide;

wherein 1 to 6 residues are alanine substituted;

wherein the peptide comprises at least one of substitutions: H275E and S279D.

wherein the peptide comprises one or more D-amino acids, L-β-homo amino acids, D-β-homo amino acids, or N-methylated amino acids;

comprising the D-retro-inverso sequence, particularly, RRQRRKKKRGY-GG-DHWIEFTANFV (SEQ ID NO:08);

wherein the peptide is acetylated, acylated, formylated, amidated, phosphorylated, sulfated or glycosylated;

comprising an N-terminal acetyl, formyl, myristoyl, palmitoyl, carboxyl or 2-furosyl group, and/or a C-terminal hydroxyl, amide, ester or thioester group; and/or wherein the peptide is cyclized.

The invention also provides pharmaceutical compositions comprising a subject compound in unit dosage, administrable form, and methods of inducing autophagy, comprising administering to a person in need thereof an effective amount of a subject compound or composition.

The invention includes all combinations of the recited particular embodiments as if each combination had been laboriously separately recited.

DESCRIPTION OF PARTICULAR EMBODIMENTS OF THE INVENTION

In one aspect the invention is an autophagy-inducing compound comprising an autophagy-inducing peptide comprising Beclin 1 residues 270-278 (FNATFHIWH; SEQ ID NO:01, residues 2-10), or the D-retro-inverso sequence thereof, immediately N- and C-terminally flanked by moieties $R_1$ and $R_2$, respectively, wherein up to six of said residues may be substituted, $R_1$ and $R_2$ do not naturally flank the Beclin 1 residues, and F270 and F274 are optionally substituted and optionally linked.

In embodiments the peptide comprises an unsubstituted mutant sequence of Table 1, below, or the D-retro-inverso sequence thereof, immediately N- and C-terminally flanked by moieties $R_1$ and $R_2$, respectively, wherein $R_1$ and $R_2$ do not naturally flank the Beclin 1 residues.

Peptide and compound activity are tolerant to a variety of additional moieties, flanking residues, and substitutions within the defined boundaries. Peptide and compound activity are also tolerant to backbone modification and replacement, side-chain modifications, and N- and C-terminal modifications, all conventional in the art of peptide chemistry.

Chemical modifications of the peptide bonds may be used to provide increased metabolic stability against enzyme-mediated hydrolysis; for example, peptide bond replacements (peptide surrogates), such as trifluoroethylamines, can provide metabolically more stable and biologically active peptidomimetics.

Modifications to constrain the peptide backbone include, for example, cyclic peptides/peptidomimetics which can exhibit enhanced metabolic stability against exopeptidases due to protected C- and N-terminal ends. Suitable techniques for cyclization include Cys-Cys disulfide bridges, peptide macrolactam, peptide thioether, parallel and antiparallel cyclic dimers, etc.; see, e.g. PMID 22230563 (stapled peptides), PMID 23064223 (use of click variants for peptide cyclization), PMID 23133740 (optimizing PK properties of cyclic peptides: effects of side chain substitutions), PMID: 22737969 (identification of key backbone motifs for intestinal permeability, PMID 12646037 (cyclization by coupling 2-amino-d,l-dodecanoic acid (Laa) to the N terminus (LaaMII), and by replacing Asn with this lipoamino acid).

In particular embodiments F270 and F274 are substituted and linked, such as wherein the side chains of F270 and F274 replaced by a linker. For example, these residues may be substituted with homocysteines connected through a disulfide bridge to generate a ring and tail cyclic peptide. In addition, the side chains of these residues can be substituted and cross-linked to form a linker, such as —CH$_2)_n$ON-HCOX(CH$_2)_m$—, wherein X is CH$_2$, NH or O, and m and n are integers 1-4, forming a lactam peptide; —CH$_2$OCH$_2$CHCHCH$_2$OCH$_2$—, forming an ether peptide; —(CH$_2)_n$CHCH(CH$_2)_m$—, forming a stapled peptide. The linkers may incorporate additional atoms, heteroatoms, or other functionalities, and are typically generated from reactive side chain at F270 and F274. The crosslinkable moieties may include additional α-carbon substitutions, such as optionally substituted, optionally hetero-lower alkyl, particularly optionally substituted, optionally hetero-methyl, ethyl, propyl and butyl. Exemplary crosslinkable moieties include:

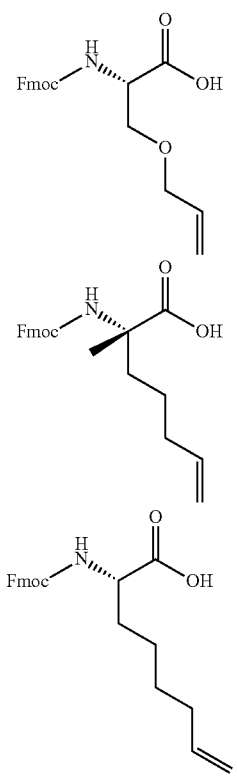

Other suitable modifications include acetylation, acylation (e.g. lipopeptides), formylation, amidation, phosphorylation (on Ser, Thr and/or Tyr), etc. which can be used to improve peptide bioavailability and/or activity, glycosylation, sulfonation, incorporation of chelators (e.g. DOTA, DPTA), etc. PEGylation can be used to increase peptide solubility, bioavailability, in vivo stability and/or decrease immunogenicity, and includes a variety of different PEGs: HiPEG, branched and forked PEGs, releasable PEGs; heterobifunctional PEG (with endgroup N-Hydroxysuccinimide (NHS) esters, maleimide, vinyl sulfone, pyridyl disulfide, amines, and carboxylic acids), etc.

Suitable terminal modifications include N-terminal acetyl, formyl, myristoyl, palmitoyl, carboxyl and 2-furosyl, and C-terminal hydroxyl, amide, ester and thioester groups, which can make the peptide more closely mimic the charge state in the native protein, and/or make it more stable to degradation from exopeptidases.

The peptides may also contain atypical or unnatural amino acids, including D-amino acids, L-β-homo amino acids, D-β-homo amino acids, N-methylated amino acids, etc.

A wide variety of flanking moieties $R_1$ and/or $R_2$ may be employed, such as affinity tags, transduction domains, homing or targeting moieties, labels, or other functional groups, such as to improve bioavailability and/or activity, and/or provide additional properties.

One useful class of such moieties include transduction domains which facilitate cellular penetrance or uptake, such as protein-derived (e.g. tat, smac, pen, pVEC, bPrPp, PIs1, VP22, M918, pep-3); chimeric (e.g. TP, TP10, MPGΔ) or synthetic (e.g. MAP, Pep-1, Oligo Arg) cell-penetrating peptides; see, e.g. "Peptides as Drugs: Discovery and Development", Ed. Bernd Groner, 2009 WILEY-VCH Verlag GmbH & Co, KGaA, Weinheim, esp. Chap 7: "The Internalization Mechanisms and Bioactivity of the Cell-Penetrating Peptides", Mats Hansen, Elo Eriste, and Ulo Langel, pp. 125-144.

Another class are homing biomolecules, such as RGD-4C (CCDCRGDCFC; SEQ ID NO:04), NGR (CCNGRC; SEQ ID NO:05), CREKA, LyP-1 (CGNKRTRGC; SEQ ID NO:06), F3, SMS (SMSIARL; SEQ ID NO:07), IF7, and H2009.1 (Li et al. Bioorg Med Chem. 2011 Sep. 15; 19(18): 5480-9), particularly cancer cell homing or targeting biomolecules, wherein suitable examples are known in the art, e.g. e.g. Homing peptides as targeted delivery vehicles, Pirjo Laakkonen and Kirsi Vuorinen, Integr. Biol., 2010, 2, 326-337; Mapping of Vascular ZIP Codes by Phage Display, Teesalu T, Sugahara K N, Ruoslahti E., Methods Enzymol. 2012; 503:35-56.

Other useful classes of such moieties include stabilizing agents, such as PEG, oligo-N-methoxyethylglycine (NMEG), albumin, an albumin-binding protein, or an immunoglobulin Fc domain; affinity tags, such as immuno-tags, biotin, lectins, chelators, etc.; labels, such as optical tags (e.g. Au particles, nanodots), chelated lanthanides, fluorescent dyes (e.g. FITC, FAM, rhodamines), FRET acceptor/donors, etc.

The moieties, tags and functional groups may be coupled to the peptide through linkers or spacers known in the art, such as polyglycine, ε-aminocaproic, etc.

The compound and/or peptide can also be presented as latent or activatable forms, such as a prodrug, wherein the active peptide is metabolically liberated; for example, release of the linear peptide from cyclic prodrugs prepared with an acyloxyalkoxy promoiety (prodrug 1) or a 3-(2'-hydroxy-4',6'-dimethylphenyl)-3,3-dimethyl propionic acid promoiety (prodrug 2) of the compound).

Particular embodiments include all combinations of particular embodiments, as though each had be separately set forth; for example, wherein the peptide is N-terminally flanked with T-N and C-terminally flanked by T, the first moiety is a tat protein transduction domain linked to the peptide through a diglycine linker; and wherein the peptide is N-terminally flanked with T-N and C-terminally flanked by T, the first moiety is a tetrameric integrin α(v)β(6)-binding peptide known as H2009.1, linked to the peptide through a maleimide—PEG(3) linker.

In another aspect the invention provides a method of inducing autophagy, comprising administering to a person in need thereof an effective amount of a subject compound or composition. Applications broadly encompass persons in need of enhanced autophagy, and include diseases and pathologies where the upregulation of autophagy is therapeutically beneficial, including infection with intracellular pathogens, neurodegenerative diseases, cancers, cardiomyopathy, and aging.

Autophagy can be detected directly, indirectly or inferentially by conventional assays, such as disclosed and/or exemplified herein, including biochemically (by assessing the generation of Atg8-PE or LC3-II or the degradation of p62) or microscopically (e.g. by observing the localization pattern of fluorescently tagged Atg8 or LC3).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

EXAMPLES

We used the beclin 1 ECD structure as a basis for rational design and optimizing the beclin 1 peptide as a therapeutic.

A sequence alignment of Atg6/beclin 1 orthologues revealed two conserved aromatic residues (F270 and F274) within the Tat-beclin 1 peptide that are required for its autophagy-inducing activity [1]. When mapped to the beclin 1 ECD structure, these aromatic side chains interact in a T-shaped geometry and help to position the intervening residues in a surface-exposed loop. We inferred that the aromatic residues play an analogous role in the Tat-beclin 1 peptide, thus contributing to its structural stability, and that replacing this aromatic interaction with a more permanent chemical linkage should further improve conformational stability [2]. For example, the two aromatics could be replaced with homocysteines that exhibit a similar length as the native sidechains and can be cyclized to form a stabilized ring-and-tail peptide structure. Similar biologically active cyclic peptide structures exist in nature, such as the 6-amino acid ring and 3 amino acid tail structure of the peptide hormone vasopressin [3] or the 8-amino acid ring and 13 amino acid tail structure of the RNA polymerase inhibiting peptide microcin [4].

To further assess the components of the beclin 1 peptide required for autophagy-inducing activity, a series of shorter peptides were developed. Activity was measured by biochemical autophagy assays including western blot detection of p62 (a protein degraded by autophagy) and western blot detection of the conversion of LC3-I into LC3-II (the lipidated autophagosome-associated form of LC3). 10 micromolar concentration of Tat-GG-VFNATFEIWHD (SEQ ID NO:09) results in increased p62 degradation and increased LC3-II conversion as compared to 10 micromolar concentrations of the Tat-Beclin 1 compound; see, Shoji-Kawata et al. (2013), below.

The Tat-beclin 1 peptides could tolerate losing the two N-terminal beclin 1 amino acids, but lost potency with the removal of the third N-terminal residue. The two required structural residues (F270 and F274) make up the N-terminal half of the beclin 1 peptide, forming a surface loop that may dictate activity. TAT-fusions corresponding to this N-terminal half were tested alone and with the C-terminal half added in trans. Neither of these peptides, nor their combination, was able to induce autophagy. This lack of activity suggests a requirement for some component of the C-terminus in addition to the N-terminal aromatic stabilized loop. In the ECD structure, the C-terminal residues following the D (corresponding to S279 mutated for solubility) are largely buried and unlikely to contribute directly to an interaction surface. Accordingly, omission of these five C-terminal residues from the beclin 1 peptide yielded the most potent inducer of autophagy thus tested. The surface components of the minimal peptide include 1) the N-terminal V 2) the aromatic intervening NAT and 2) the C-terminal WH. These residues are inferred to contribute to a binding surface in the peptide that mimics the ECD and is required for induction of autophagy by the peptide.

We used targeted mutagenesis of amino acids that are predicted to be important based on their substitution patterns during evolution [PMID 8609628; 15037084]. This approach has been successfully applied to design point mutants that modify the activity of functional sites [PMID 20385837] and that selectively block function [PMID 16280323]. We similarly use a series of three or four different mutations at each position to probe both conservative to non-conservative substitutions based on standard transition matrices [PMID 1438297], using mutations to residues predicted to be less important as negative controls to map out efficiently the key binding residues in the minimal peptide. To enhance potency and identify activity determinants we can increasingly perturb residues through increasingly less conservative substitutions, for example, V269 to I, L, M then A, or I276 to V, L, F, etc. We also use scanning mutagenesis to systematically change each residue one at a time.

F270 and F274 function to restrict the conformational flexibility of the intervening residues and reduce the entropy cost of binding. We prepared a number of more chemically-stable linkers via standard solid-phase peptide synthesis. For instance, replacement of F270 with a lysine and F274 with an aspartic or glutamic acid residue allows the synthesis of macrocyclic lactam peptides of incrementally-larger ring size. Even more chemically-stable linkages can be achieved through ring-closing metathesis strategies, where terminal alkene handles derived from commercial non-natural amino acids offer a chemical handle for cyclization. This latter carbon-carbon based cyclization modality is often called peptide "stapling", and has been reviewed extensively (PMID 22230563). An advantage of backbone "staples" is the reduced susceptibility of carbon-carbon linkages to proteolytic cleavage. "Click" variants derived from [3+2] cycloaddition reactions may also be used for peptide cyclization (PMID 23064223).

These various cyclization strategies enforce the bioactive conformation of the beclin peptide, and can be used to increase the cellular permeability relative to the uncyclized peptide. Peptide conformation can significantly influence the ability of macromolecules to penetrate into cells (PMID:

23133740). In particular, backbone modifications can have dramatic impact on cellular permeability, potentially creating opportunities for oral administration of cyclic peptides (PMID 22737969 and PMID 12646037). Optionally combined with retro-inverso peptide strategies to further limit amide hydrolysis (PMID 23382963), these compositions enable use the disclosed compounds as peptide therapeutics.

TABLE 1

Targeted mutagensis

| Peptide | Sequence* | SEQ ID NO | Activity |
|---|---|---|---|
| Wild-type (wt) | VFNATFEIWHD | SEQ ID NO: 03 | wt |
| Mutant 1 | CFNATFEIWHD | SEQ ID NO: 10 | ~wt |
| Mutant 2 | VWNATFEIWHD | SEQ ID NO: 11 | >wt |
| Mutant 3 | VFDATFEIWHD | SEQ ID NO: 12 | <<wt |
| Mutant 4 | VFNSTFEIWHD | SEQ ID NO: 13 | <<wt |
| Mutant 5 | VFNACFEIWHD | SEQ ID NO: 14 | <wt |
| Mutant 6 | VFNATWEIWHD | SEQ ID NO: 15 | <wt |
| Mutant 7 | VFNATFDIWHD | SEQ ID NO: 16 | ~wt |
| Mutant 8 | VFNATFELWHD | SEQ ID NO: 17 | >wt |
| Mutant 9 | VFNATFEIFHD | SEQ ID NO: 18 | ~wt |
| Mutant 10 | VFNATFEIWYD | SEQ ID NO: 19 | ~wt |
| Mutant 11 | VFNATFEIWHE | SEQ ID NO: 20 | ~wt |
| Mutant 12 | VWNATFELWHD | SEQ ID NO: 21 | ~wt |
| Mutant 13 | VYNATFEIWHD | SEQ ID NO: 22 | <wt |
| Mutant 14 | VFNATFEVWHD | SEQ ID NO: 23 | ~wt |
| Mutant 15 | VLNATFEIWHD | SEQ ID NO: 24 | ~wt |
| Mutant 16 | VFNATFEMWHD | SEQ ID NO: 25 | ~wt |
| Mutant 17 | VWNATFHIWHD | SEQ ID NO: 26 | >>wt |
| Mutant 18 | VFNATFEFWHD | SEQ ID NO: 27 | ~wt |
| Mutant 19 | VFNATFEYWHD | SEQ ID NO: 28 | ~wt |

TABLE 1-continued

Targeted mutagensis

| Peptide | Sequence* | SEQ ID NO | Activity |
|---|---|---|---|
| Mutant 20 | VFNATFERWHD | SEQ ID NO: 29 | ~wt |
| Mutant 21 | FNATFEIWHD | SEQ ID NO: 30 | >wt |
| Mutant 25 | VFNATFEIWH | SEQ ID NO: 31 | >wt |
| Mutant 26 | FNATFEIWH | SEQ ID NO: 32 | >>wt |
| Mutant 27 | WNATFHIWH | SEQ ID NO: 33 | >>wt |
| Mutant 28 | VWNATFHIWH | SEQ ID NO: 34 | >>wt |
| Mutant 29 | WNATFHIWHD | SEQ ID NO: 35 | >>wt |
| Mutant 30 | DHWIHFTANWV | SEQ ID NO: 36 | >>wt |

*The 11 amino acids PTD from HIV TAT and the diglycine linker are not listed; this is the same for all peptides. Mutant 17 and its derivatives are the most active, and activity is retained with the corresponding D-retro-inverso sequences (e.g. Mutant 30). Activity was measured as autophagy inducing activity, as described supra.

REFERENCES

[1] S. Shoji-Kawata, R. Sumpter, M. Leveno, G. R. Campbell, Z. Zou, L. Kinch, A. D. Wilkins, Q. Sun, K. Pallauf, D. MacDuff, C. Huerta, H. W. Virgin, J. B. Helms, R. Eerland, S. A. Tooze, R. Xavier, D. J. Lenschow, A. Yamamoto, D. King, O. Lichtarge, N. V. Grishin, S. A. Spector, D. V. Kaloyanova, B. Levine, Identification of a candidate therapeutic autophagy-inducing peptide, Nature, 494 201-206, 2013.
[2] A. Bryan, L. Joseph, J. A. Bennett, H. I. Jacobson, T. T. Andersen, Design and synthesis of biologically active peptides: a 'tail' of amino acids can modulate activity of synthetic cyclic peptides, Peptides, 32 2504-2510.
[3] J. P. Rose, C. K. Wu, C. D. Hsiao, E. Breslow, B. C. Wang, Crystal structure of the neurophysin-oxytocin complex, Nat Struct Biol, 3 (1996) 163-169.
[4] K. J. Rosengren, R. J. Clark, N. L. Daly, U. Goransson, A. Jones, D. J. Craik, Microcin J25 has a threaded sidechain-to-backbone ring structure and not a head-to-tail cyclized backbone, J Am Chem Soc, 125 (2003) 12464-12474.

What is claimed is:

1. An autophagy-inducing compound comprising an autophagy-inducing 9, 10 or 11-mer peptide of Beclin 1, and no more of Beclin 1 than the 9, 10 or 11-mer peptide, the peptide comprising Beclin 1 residue 269 or 270 to Beclin 1 residue 278 or 279, wherein Beclin 1 residues 269-279 is VFNATFHIWHS (SEQ ID NO:01), wherein up to six of said residues may be substituted, and wherein:

(a) F270 and F274 are substituted or linked;

(b) the peptide is cyclized;

(c) the peptide is N-terminally flanked by moiety $R_1$, and $R_1$ comprises a transduction domain, a homing peptide, or a serum stabilizing agent; or (d) the peptide comprises a sequence, unsubstituted, selected from:

| Peptide   | Sequence    | SEQ ID NO      |
|-----------|-------------|----------------|
| Mutant 1  | CFNATFEIWHD | SEQ ID NO: 10; |
| Mutant 2  | VWNATFEIWHD | SEQ ID NO: 11; |
| Mutant 3  | VFDATFEIWHD | SEQ ID NO: 12; |
| Mutant 4  | VFNSTFEIWHD | SEQ ID NO: 13; |
| Mutant 5  | VFNACFEIWHD | SEQ ID NO: 14; |
| Mutant 6  | VFNATWEIWHD | SEQ ID NO: 15; |
| Mutant 7  | VFNATFDIWHD | SEQ ID NO: 16; |
| Mutant 8  | VFNATFELWHD | SEQ ID NO: 17; |
| Mutant 9  | VFNATFEIFHD | SEQ ID NO: 18; |

-continued

| Peptide | Sequence | SEQ ID NO |
|---|---|---|
| Mutant 10 | VFNATFEIWYD | SEQ ID NO: 19; |
| Mutant 11 | VFNATFEIWHE | SEQ ID NO: 20; |
| Mutant 12 | VWNATFELWHD | SEQ ID NO: 21; |
| Mutant 13 | VYNATFEIWHD | SEQ ID NO: 22; |
| Mutant 14 | VFNATFEVWHD | SEQ ID NO: 23; |
| Mutant 15 | VLNATFEIWHD | SEQ ID NO: 24; |
| Mutant 16 | VFNATFEMWHD | SEQ ID NO: 25; |
| Mutant 17 | VWNATFHIWHD | SEQ ID NO: 26; |
| Mutant 18 | VFNATFEFWHD | SEQ ID NO: 27; |
| Mutant 19 | VFNATFEYWHD | SEQ ID NO: 28; |
| Mutant 20 | VFNATFERWHD | SEQ ID NO: 29; |
| Mutant 21 | FNATFEIWHD | SEQ ID NO: 30; |
| Mutant 25 | VFNATFEIWH | SEQ ID NO: 31; |
| Mutant 26 | FNATFEIWH | SEQ ID NO: 32; |
| Mutant 27 | WNATFHIWH | SEQ ID NO: 33; |
| Mutant 28 | VWNATFHIWH | SEQ ID NO: 34; and |
| Mutant 29 | WNATFHIWHD | SEQ ID NO: 35. |

2. The compound of claim 1 wherein the peptide comprises a sequence, unsubstituted, selected from:

| Peptide | Sequence | SEQ ID NO |
|---|---|---|
| Mutant 1 | CFNATFEIWHD | SEQ ID NO: 10; |
| Mutant 2 | VWNATFEIWHD | SEQ ID NO: 11; |
| Mutant 3 | VFDATFEIWHD | SEQ ID NO: 12; |
| Mutant 4 | VFNSTFEIWHD | SEQ ID NO: 13; |
| Mutant 5 | VFNACFEIWHD | SEQ ID NO: 14; |
| Mutant 6 | VFNATWEIWHD | SEQ ID NO: 15; |
| Mutant 7 | VFNATFDIWHD | SEQ ID NO: 16; |
| Mutant 8 | VFNATFELWHD | SEQ ID NO: 17; |
| Mutant 9 | VFNATFEIFHD | SEQ ID NO: 18; |
| Mutant 10 | VFNATFEIWYD | SEQ ID NO: 19; |
| Mutant 11 | VFNATFEIWHE | SEQ ID NO: 20; |
| Mutant 12 | VWNATFELWHD | SEQ ID NO: 21; |
| Mutant 13 | VYNATFEIWHD | SEQ ID NO: 22; |
| Mutant 14 | VFNATFEVWHD | SEQ ID NO: 23; |
| Mutant 15 | VLNATFEIWHD | SEQ ID NO: 24; |
| Mutant 16 | VFNATFEMWHD | SEQ ID NO: 25; |
| Mutant 17 | VWNATFHIWHD | SEQ ID NO: 26; |
| Mutant 18 | VFNATFEFWHD | SEQ ID NO: 27; |
| Mutant 19 | VFNATFEYWHD | SEQ ID NO: 28; |
| Mutant 20 | VFNATFERWHD | SEQ ID NO: 29; |
| Mutant 21 | FNATFEIWHD | SEQ ID NO: 30; |
| Mutant 25 | VFNATFEIWH | SEQ ID NO: 31; |
| Mutant 26 | FNATFEIWH | SEQ ID NO: 32; |
| Mutant 27 | WNATFHIWH | SEQ ID NO: 33; |
| Mutant 28 | VWNATFHIWH | SEQ ID NO: 34; and |
| Mutant 29 | WNATFHIWHD | SEQ ID NO: 35. |

3. The compound of claim 1 wherein the peptide comprises the sequence VWNATFHIWHD (SEQ ID NO:26).

4. The compound of claim 1, wherein the peptide is N-terminally flanked by moiety $R_1$, and $R_1$ comprises a transduction domain, a homing peptide, or a serum stabilizing agent.

5. The compound of claim 1, wherein the peptide is N-terminally flanked by moiety $R_1$, and $R_1$ comprises a transduction domain that is:
   a protein-derived cell-penetrating peptide selected from tat, smac, pen, pVEC, bPrPp, PIs1, VP22, M918 and pep-3;
   a chimeric cell-penetrating peptide selected from TP, TP10 and MPGΔ; or
   a synthetic cell-penetrating peptide selected from MAP, Pep-1, and oligo Arg.

6. The compound of claim 1, wherein the peptide is N-terminally flanked by moiety $R_1$, and $R_1$ comprises a transduction domain that is a protein-derived cell-penetrating peptide that is tat.

7. The compound of claim 1, wherein the peptide is N-terminally flanked by moiety $R_1$, and $R_1$ comprises a transduction domain that is a synthetic cell-penetrating peptide that is oligo Arg.

8. The compound of claim 1, wherein the peptide is N-terminally flanked by moiety $R_1$, and $R_1$ comprises a transduction domain that is a protein-derived cell-penetrating peptide that is tat, or a synthetic cell-penetrating peptide that is oligo Arg, and the peptide is C-terminally flanked by moiety $R_2$, and $R_2$ is carboxyl or $R_2$ comprises an affinity tag or detectable label.

9. The compound of claim 1, wherein the peptide is N-terminally flanked through a diglycine linker.

10. The compound of claim 1 wherein the peptide is C-terminally flanked by moiety $R_2$, and $R_2$ is carboxyl or $R_2$ comprises an affinity tag or detectable label.

11. The compound of claim 1 wherein the peptide is C-terminally flanked by moiety $R_2$, and $R_2$ is carboxyl.

12. The compound of claim 1, wherein:
   the peptide comprises the sequence VWNATFHIWHD (SEQ ID NO:26);
   the peptide is N-terminally flanked by moiety $R_1$, and $R_1$ comprises a transduction domain that is a protein-derived cell-penetrating peptide that is tat;
   the peptide is N-terminally flanked through a diglycine linker; and
   the peptide is C-terminally flanked by moiety $R_2$, and $R_2$ is carboxyl.

13. The compound of claim 1, wherein:
the peptide comprises the sequence VWNATFHIWHD (SEQ ID NO:26);
the peptide is N-terminally flanked by moiety $R_1$, and $R_1$ comprises a transduction domain that is a synthetic cell-penetrating peptide that is oligo Arg;
the peptide is N-terminally flanked through a diglycine linker; and
the peptide is C-terminally flanked by moiety $R_2$, and $R_2$ is carboxyl.

14. The compound of claim 1 wherein F270 and/or F274 are substituted or linked.

15. The compound of claim 1 wherein:
a) F270 and F274 are substituted with crosslinkable moieties and/or linked, and each optionally comprises an additional α-carbon substitution selected from substituted, optionally hetero-lower alkyl, particularly optionally substituted, optionally hetero-methyl, ethyl, propyl and butyl; or
b) F270 and F274 are substituted with homocysteines connected through a disulfide bridge to generate a ring and tail cyclic peptide.

16. The compound of claim 1 wherein side chains of F270 and F274 are replaced by a linker:
—$(CH_2)_n$ONHCOX$(CH_2)_m$—, wherein X is $CH_2$, NH or O, and m and n are integers 1-4, forming a lactam peptide;
—$CH_2OCH_2CHCHCH_2OCH_2$—, forming an ether peptide; or
—$(CH_2)_n$CHCH$(CH_2)_m$—, forming a stapled peptide.

17. The compound of claim 1 wherein the peptide is cyclized.

18. The compound of claim 1 wherein:
1 to 6 residues are alanine substituted;
the peptide comprises at least one of substitutions: H275E and S279D; or
the peptide comprises one or more D-amino acids, L-β-homo amino acids, D-β-homo amino acids, or N-methylated amino acids;
the peptide is acetylated, acylated, formylated, amidated, phosphorylated, sulfated or glycosylated; or
the compound comprises an N-terminal acetyl, formyl, myristoyl, palmitoyl, carboxyl or 2-furosyl group, and/or a C-terminal hydroxyl, amide, ester or thioester group.

19. A pharmaceutical composition comprising a compound of claim 1 in unit dosage, administrable form.

20. A method of inducing autophagy, comprising administering to a person in need thereof an effective amount of a compound of claim 1.

* * * * *

SEQUENCE LISTING

<160> NUMBER OF SEQ ID NOS: 36

<210> SEQ ID NO 1
<211> LENGTH: 11
<212> TYPE: PRT
<213> ORGANISM: Artificial sequence
<220> FEATURE:
<223> OTHER INFORMATION: Synthetic

<400> SEQUENCE: 1

Val Phe Asn Ala Thr Phe His Ile Trp His Ser
1               5                   10

<210> SEQ ID NO 2
<211> LENGTH: 11
<212> TYPE: PRT
<213> ORGANISM: Artificial sequence
<220> FEATURE:

<223> OTHER INFORMATION: Synthetic

<400> SEQUENCE: 2

Val Phe Asn Ala Thr Phe His Ile Trp His Asp
1               5                   10

<210> SEQ ID NO 3
<211> LENGTH: 11
<212> TYPE: PRT
<213> ORGANISM: Artificial sequence
<220> FEATURE:
<223> OTHER INFORMATION: Synthetic

<400> SEQUENCE: 3

Val Phe Asn Ala Thr Phe Glu Ile Trp His Asp
1               5                   10

<210> SEQ ID NO 4
<211> LENGTH: 10
<212> TYPE: PRT
<213> ORGANISM: Artificial sequence
<220> FEATURE:
<223> OTHER INFORMATION: Synthetic

<400> SEQUENCE: 4

Cys Cys Asp Cys Arg Gly Asp Cys Phe Cys
1               5                   10

<210> SEQ ID NO 5
<211> LENGTH: 6
<212> TYPE: PRT
<213> ORGANISM: Artificial sequence
<220> FEATURE:
<223> OTHER INFORMATION: Synthetic

<400> SEQUENCE: 5

Cys Cys Asn Gly Arg Cys
1               5

<210> SEQ ID NO 6
<211> LENGTH: 9
<212> TYPE: PRT
<213> ORGANISM: Artificial sequence
<220> FEATURE:
<223> OTHER INFORMATION: Synthetic

<400> SEQUENCE: 6

Cys Gly Asn Lys Arg Thr Arg Gly Cys
1               5

<210> SEQ ID NO 7
<211> LENGTH: 7
<212> TYPE: PRT
<213> ORGANISM: Artificial sequence
<220> FEATURE:
<223> OTHER INFORMATION: Synthetic

<400> SEQUENCE: 7

Ser Met Ser Ile Ala Arg Leu
1               5

<210> SEQ ID NO 8
<211> LENGTH: 24
<212> TYPE: PRT
<213> ORGANISM: Artificial sequence
<220> FEATURE:
<223> OTHER INFORMATION: Synthetic

<400> SEQUENCE: 8

Arg Arg Gln Arg Arg Lys Lys Lys Arg Gly Tyr Gly Gly Asp His Trp
1               5                   10                  15

Ile Glu Phe Thr Ala Asn Phe Val
            20

<210> SEQ ID NO 9
<211> LENGTH: 13
<212> TYPE: PRT
<213> ORGANISM: Artificial sequence
<220> FEATURE:
<223> OTHER INFORMATION: Synthetic

<400> SEQUENCE: 9

Gly Gly Val Phe Asn Ala Thr Phe Glu Ile Trp His Asp
1               5                   10

<210> SEQ ID NO 10
<211> LENGTH: 11
<212> TYPE: PRT
<213> ORGANISM: Artificial sequence
<220> FEATURE:
<223> OTHER INFORMATION: Synthetic

<400> SEQUENCE: 10

Cys Phe Asn Ala Thr Phe Glu Ile Trp His Asp
1               5                   10

<210> SEQ ID NO 11
<211> LENGTH: 11
<212> TYPE: PRT
<213> ORGANISM: Artificial sequence
<220> FEATURE:
<223> OTHER INFORMATION: Synthetic

<400> SEQUENCE: 11

Val Trp Asn Ala Thr Phe Glu Ile Trp His Asp
1               5                   10

<210> SEQ ID NO 12
<211> LENGTH: 11
<212> TYPE: PRT
<213> ORGANISM: Artificial sequence
<220> FEATURE:
<223> OTHER INFORMATION: Synthetic

<400> SEQUENCE: 12

Val Phe Asp Ala Thr Phe Glu Ile Trp His Asp
1               5                   10

<210> SEQ ID NO 13
<211> LENGTH: 11
<212> TYPE: PRT
<213> ORGANISM: Artificial sequence
<220> FEATURE:
<223> OTHER INFORMATION: Synthetic

<400> SEQUENCE: 13

Val Phe Asn Ser Thr Phe Glu Ile Trp His Asp
1               5                   10

<210> SEQ ID NO 14
<211> LENGTH: 11
<212> TYPE: PRT
<213> ORGANISM: Artificial sequence

```
<220> FEATURE:
<223> OTHER INFORMATION: Synthetic

<400> SEQUENCE: 14

Val Phe Asn Ala Cys Phe Glu Ile Trp His Asp
1               5                   10

<210> SEQ ID NO 15
<211> LENGTH: 11
<212> TYPE: PRT
<213> ORGANISM: Artificial sequence
<220> FEATURE:
<223> OTHER INFORMATION: Synthetic

<400> SEQUENCE: 15

Val Phe Asn Ala Thr Trp Glu Ile Trp His Asp
1               5                   10

<210> SEQ ID NO 16
<211> LENGTH: 11
<212> TYPE: PRT
<213> ORGANISM: Artificial sequence
<220> FEATURE:
<223> OTHER INFORMATION: Synthetic

<400> SEQUENCE: 16

Val Phe Asn Ala Thr Phe Asp Ile Trp His Asp
1               5                   10

<210> SEQ ID NO 17
<211> LENGTH: 11
<212> TYPE: PRT
<213> ORGANISM: Artificial sequence
<220> FEATURE:
<223> OTHER INFORMATION: Synthetic

<400> SEQUENCE: 17

Val Phe Asn Ala Thr Phe Glu Leu Trp His Asp
1               5                   10

<210> SEQ ID NO 18
<211> LENGTH: 11
<212> TYPE: PRT
<213> ORGANISM: Artificial sequence
<220> FEATURE:
<223> OTHER INFORMATION: Synthetic

<400> SEQUENCE: 18

Val Phe Asn Ala Thr Phe Glu Ile Phe His Asp
1               5                   10

<210> SEQ ID NO 19
<211> LENGTH: 11
<212> TYPE: PRT
<213> ORGANISM: Artificial sequence
<220> FEATURE:
<223> OTHER INFORMATION: Synthetic

<400> SEQUENCE: 19

Val Phe Asn Ala Thr Phe Glu Ile Trp Tyr Asp
1               5                   10

<210> SEQ ID NO 20
<211> LENGTH: 11
<212> TYPE: PRT
<213> ORGANISM: Artificial sequence
<220> FEATURE:
```

<223> OTHER INFORMATION: Synthetic

<400> SEQUENCE: 20

Val Phe Asn Ala Thr Phe Glu Ile Trp His Glu
1               5                   10

<210> SEQ ID NO 21
<211> LENGTH: 11
<212> TYPE: PRT
<213> ORGANISM: Artificial sequence
<220> FEATURE:
<223> OTHER INFORMATION: Synthetic

<400> SEQUENCE: 21

Val Trp Asn Ala Thr Phe Glu Leu Trp His Asp
1               5                   10

<210> SEQ ID NO 22
<211> LENGTH: 11
<212> TYPE: PRT
<213> ORGANISM: Artificial sequence
<220> FEATURE:
<223> OTHER INFORMATION: Synthetic

<400> SEQUENCE: 22

Val Tyr Asn Ala Thr Phe Glu Ile Trp His Asp
1               5                   10

<210> SEQ ID NO 23
<211> LENGTH: 11
<212> TYPE: PRT
<213> ORGANISM: Artificial sequence
<220> FEATURE:
<223> OTHER INFORMATION: Synthetic

<400> SEQUENCE: 23

Val Phe Asn Ala Thr Phe Glu Val Trp His Asp
1               5                   10

<210> SEQ ID NO 24
<211> LENGTH: 11
<212> TYPE: PRT
<213> ORGANISM: Artificial sequence
<220> FEATURE:
<223> OTHER INFORMATION: Synthetic

<400> SEQUENCE: 24

Val Leu Asn Ala Thr Phe Glu Ile Trp His Asp
1               5                   10

<210> SEQ ID NO 25
<211> LENGTH: 11
<212> TYPE: PRT
<213> ORGANISM: Artificial sequence
<220> FEATURE:
<223> OTHER INFORMATION: Synthetic

<400> SEQUENCE: 25

Val Phe Asn Ala Thr Phe Glu Met Trp His Asp
1               5                   10

<210> SEQ ID NO 26
<211> LENGTH: 11
<212> TYPE: PRT
<213> ORGANISM: Artificial sequence
<220> FEATURE:
<223> OTHER INFORMATION: Synthetic

<400> SEQUENCE: 26

Val Trp Asn Ala Thr Phe His Ile Trp His Asp
1               5                   10

<210> SEQ ID NO 27
<211> LENGTH: 11
<212> TYPE: PRT
<213> ORGANISM: Artificial sequence
<220> FEATURE:
<223> OTHER INFORMATION: Synthetic

<400> SEQUENCE: 27

Val Phe Asn Ala Thr Phe Glu Phe Trp His Asp
1               5                   10

<210> SEQ ID NO 28
<211> LENGTH: 11
<212> TYPE: PRT
<213> ORGANISM: Artificial sequence
<220> FEATURE:
<223> OTHER INFORMATION: Synthetic

<400> SEQUENCE: 28

Val Phe Asn Ala Thr Phe Glu Tyr Trp His Asp
1               5                   10

<210> SEQ ID NO 29
<211> LENGTH: 11
<212> TYPE: PRT
<213> ORGANISM: Artificial sequence
<220> FEATURE:
<223> OTHER INFORMATION: Synthetic

<400> SEQUENCE: 29

Val Phe Asn Ala Thr Phe Glu Arg Trp His Asp
1               5                   10

<210> SEQ ID NO 30
<211> LENGTH: 10
<212> TYPE: PRT
<213> ORGANISM: Artificial sequence
<220> FEATURE:
<223> OTHER INFORMATION: Synthetic

<400> SEQUENCE: 30

Phe Asn Ala Thr Phe Glu Ile Trp His Asp
1               5                   10

<210> SEQ ID NO 31
<211> LENGTH: 10
<212> TYPE: PRT
<213> ORGANISM: Artificial sequence
<220> FEATURE:
<223> OTHER INFORMATION: Synthetic

<400> SEQUENCE: 31

Val Phe Asn Ala Thr Phe Glu Ile Trp His
1               5                   10

<210> SEQ ID NO 32
<211> LENGTH: 9
<212> TYPE: PRT
<213> ORGANISM: Artificial sequence
<220> FEATURE:
<223> OTHER INFORMATION: Synthetic

```
<400> SEQUENCE: 32

Phe Asn Ala Thr Phe Glu Ile Trp His
1               5

<210> SEQ ID NO 33
<211> LENGTH: 9
<212> TYPE: PRT
<213> ORGANISM: Artificial sequence
<220> FEATURE:
<223> OTHER INFORMATION: Synthetic

<400> SEQUENCE: 33

Trp Asn Ala Thr Phe His Ile Trp His
1               5

<210> SEQ ID NO 34
<211> LENGTH: 10
<212> TYPE: PRT
<213> ORGANISM: Artificial sequence
<220> FEATURE:
<223> OTHER INFORMATION: Synthetic

<400> SEQUENCE: 34

Val Trp Asn Ala Thr Phe His Ile Trp His
1               5                   10

<210> SEQ ID NO 35
<211> LENGTH: 10
<212> TYPE: PRT
<213> ORGANISM: Artificial sequence
<220> FEATURE:
<223> OTHER INFORMATION: Synthetic

<400> SEQUENCE: 35

Trp Asn Ala Thr Phe His Ile Trp His Asp
1               5                   10

<210> SEQ ID NO 36
<211> LENGTH: 11
<212> TYPE: PRT
<213> ORGANISM: Artificial sequence
<220> FEATURE:
<223> OTHER INFORMATION: Synthetic

<400> SEQUENCE: 36

Asp His Trp Ile His Phe Thr Ala Asn Trp Val
1               5                   10
```